United States Patent [19]

Patel et al.

[11] Patent Number: 5,084,387
[45] Date of Patent: Jan. 28, 1992

[54] MICROBIOLOGICAL HYDROLYSIS FOR THE PREPARATION OF (EXO,EXO)-7-OXABICYCLO(2.2.1) HEPTANE-2,3, MONOACYL ESTER DIMETHANOL

[75] Inventors: Ramesh N. Patel, Bridgewater; Laszlo J. Szarka, East Brunswick; John K. Thottathil, Robbinsville, all of N.J.; David Kronenthal, Yardley, Pa.

[73] Assignee: E. R. Squibb & Sons, Inc., Princeton, N.J.

[21] Appl. No.: 629,780

[22] Filed: Dec. 18, 1990

[51] Int. Cl.$^5$ ............... C12P 17/02; C12R 1/38; C12N 9/18
[52] U.S. Cl. .................. 435/123; 435/197; 435/874; 549/463
[58] Field of Search ............ 435/123, 196, 197, 874, 435/875, 876, 877; 549/463

[56] References Cited

U.S. PATENT DOCUMENTS

| | | | |
|---|---|---|---|
| 4,413,054 | 3/1979 | Sprague | 260/346 |
| 4,663,336 | 5/1987 | Nakane et al. | 514/381 |
| 4,732,853 | 3/1988 | Whitesides et al. | 435/123 |
| 4,957,867 | 9/1980 | Minai et al. | 435/135 |

FOREIGN PATENT DOCUMENTS 2156892  6/1990  Japan ................. 435/876

OTHER PUBLICATIONS

G. Guanti et al., Tetrahedron Letters, 27, 4639 (1986).
R. Bloch et al., Tetrahedron Letters, 26, 4087 (1985).
J. Bryan Jones et al., Can. J. Chem., vol. 62, 2578-2582 (1984).
K. P. Lok et al., J. Am. Chem. Soc. 107, 2521-2526 (1985).

Primary Examiner—Herbert J. Lilling
Attorney, Agent, or Firm—Timothy J. Gaul

[57] ABSTRACT

Disclosed herein is a process for preparing a novel monoester of the formula

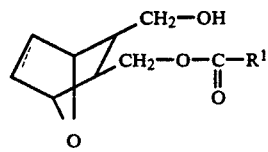

in which the associated novel diester

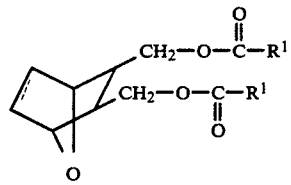

is hydrolyzed in the presence of one or more water-soluble enzymes or microorganisms capable of selectively hydrolyzing the $-O-C(O)-R^1$ group, wherein the treatment is carried out in a biphasic solvent system comprising an aqueous phase having the enzymes or microorganisms and an organic phase immiscible in water having the diester. Also disclosed is a process for preparing [1S-[1α, 2α(Z),3α,4α]]-7-[3[[[[(1-oxoheptyl)amino]acetyl]-amino]methyl-7-oxabicyclo-[2.2.1]hept-2-yl]-5-heptenoic acid using this enzymatic/microbial process.

16 Claims, No Drawings

MICROBIOLOGICAL HYDROLYSIS FOR THE PREPARATION OF (EXO,EXO)-7-OXABICYCLO(2.2.1) HEPTANE-2,3, MONOACYL ESTER DIMETHANOL

FIELD OF INVENTION

This invention relates to intermediates of and processes for preparation of thromboxane receptor antagonists.

BACKGROUND OF THE INVENTION

[1S-[1α,2α(Z),3α,4α[[-7-[3-[[[[1-oxoheptyl-)amino]acetyl]amino]methyl]-7-oxabicyclo-[2.2.1] hept-2-yl]-5-heptenoic acid is a cardiovascular agent useful, for example, in the treatment of thrombotic disease. U.S. Pat. No. 4,663,336, issued on May 5, 1987, describes a synthesis of this compound that begins with [1S-[1α,2α(Z), 3α,4α]]-7-[3-Hydroxymethyl-7-oxabicy-clo-[2.2.1]hept-2-yl]-5-heptenoic acid. Preparation of this latter compound is described in U.S. Pat. No. 4,143,054.

In the latter patent, furan and maleic anhydride react in ether solution to form compound A in Reaction Scheme 1. Compound A is reduced to form compound B, which is then reduced by, for example, a borohydride in tetrahydrofuran to form compound C. Compound C is then treated with diisobutylaluminium hydride or diisobutylborane to form compound D in racemic form.

Compound D may be resolved chemically (e.g., with d-menthol and Amberlyst ® in methylene chloride) but with yields of less than 50% of the desired (−) optical enantiomer. Moreover, the compound C-to-D conversion may be dangerous in a large scale process. The art would benefit, therefore, from a process that would allow production of compound D in high chemical yield and high optical purity that avoids the dangerous C-to-D chemical conversion and the low-yielding resolution step.

Reaction Scheme 1 (Prior Art)

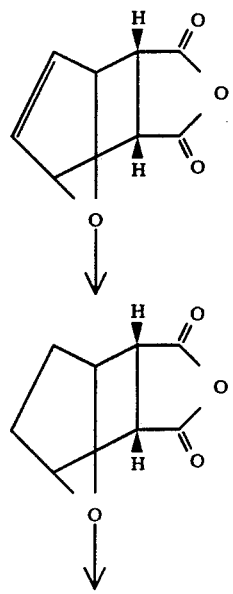

-continued
Reaction Scheme 1 (Prior Art)

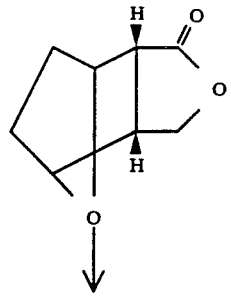

C.

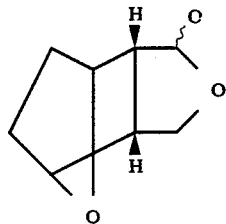

D.

BRIEF DESCRIPTION OF THE INVENTION

In the novel process of the present invention, novel compound III of Reaction Scheme 2 is prepared by hydrolyzing novel compound II in the presence of one or more water-soluble enzymes or microorganisms capable of selectively hydrolyzing the —O—C(O)—$R^1$ group, wherein the treatment is carried out in a biphasic solvent system comprising an aqueous phase having the enzymes or microorganisms and an organic phase immiscible in water having compound II. In compounds II and III and throughout this specification, $R^1$ is alkyl, aryl, cycloalkyl, aralkyl, cycloalkylalkyl, or alkaryl. This novel process is highly stereoselective, yielding compound III in greater than 99% (−) optical purity.

Further in accordance with the present invention, compound III is oxidized and hydrolyzed (and hydrogenated when it comprises a double bond) to form compound V (compound D in resolved form).

Further still in accordance with the present invention, a process is provided for preparing compound XI (see Reaction Scheme 2) using the above-described process.

Additionally, compounds II and III are novel and form an integral part of the present invention.

DETAILED DESCRIPTION OF THE INVENTION

The following definitions apply to the terms as used throughout this specification, both individually and as part of other groups.

The term "alkyl" or "alk-" as used herein refers to straight or branched chain hydrocarbon groups of 1 to 12 carbon atoms, preferably 1 to 6 carbon atoms.

The term "cycloalkyl" as used herein refers to groups having 3 to 7 carbon atoms in the ring.

The term "aryl" or "ar-" as used herein refers to monocyclic or bicyclic aromatic groups having from 6 to 10 carbon atoms in the ring portion, such as phenyl, naphthyl, and substituted phenyl or naphthyl having such substituents as nitro, halo, methyl or alkoxy.

The term "halogen" or "halo" refers to chlorine, bromine, and iodine.

The term "alkali metal" refers to lithium, sodium and potassium.
acylating agent (e.g., acetic anhydride) in an organic solvent (e.g., pyridine) at about 15° to 40° C. to form compound II.
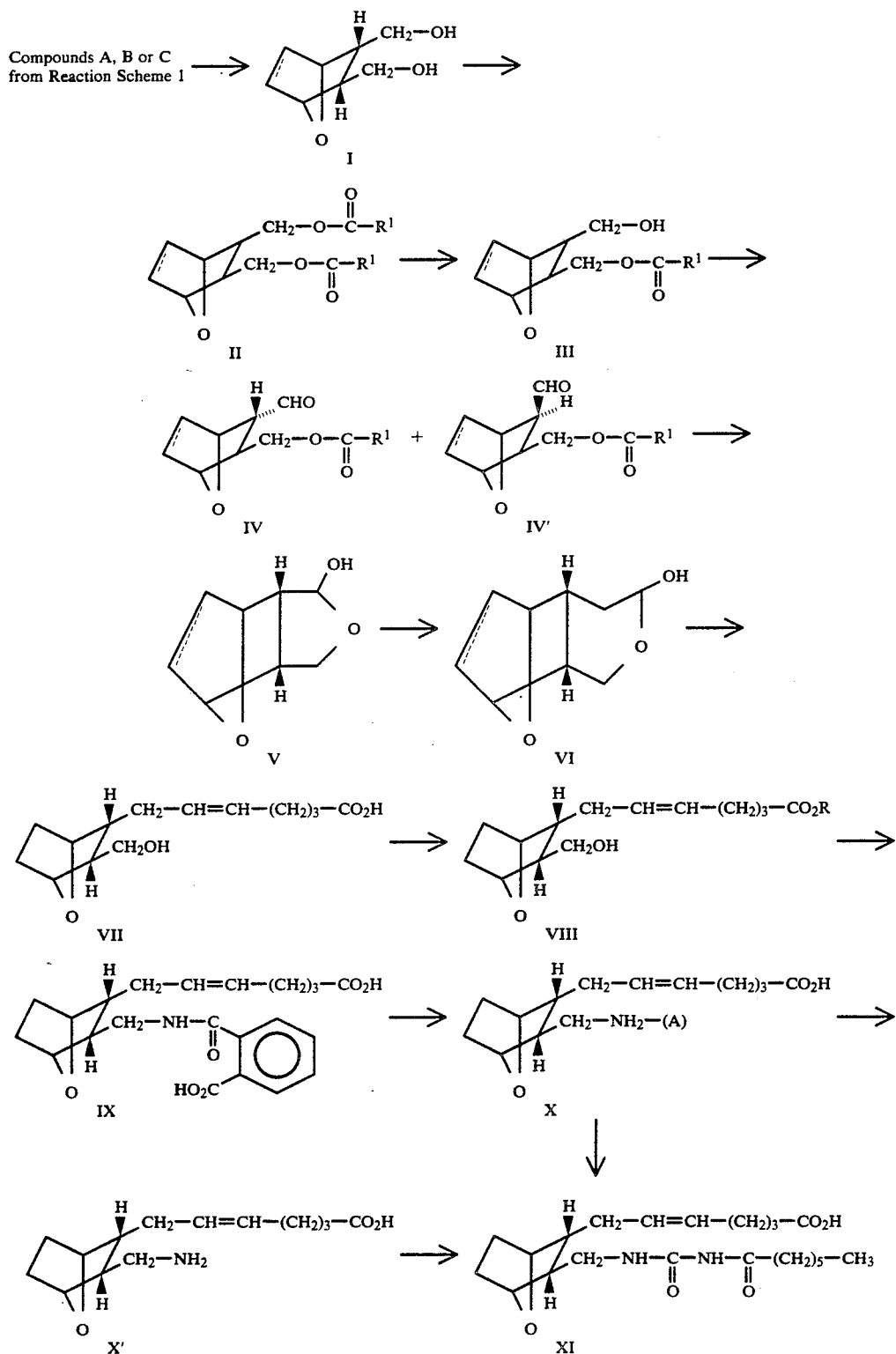
In Reaction Scheme 2, compounds A, B and C are converted to diol compound I by, for example, treatment with lithium aluminum hydride in tetrahydrofuran at about 35° to 45° C. Compound I is reacted with an Compound II is then hydrolyzed in a selective enzymatic or microbial process. The process uses water-soluble enzymes capable of asymmetric hydrolysis to provide products in a desired enantiomeric form. Especially suitable for use with the present process are the various known lipases and esterases. Pancreatin and α-chymotrypsin are also suitable. The present invention is able to utilize either the crude or purified forms of these enzymes in either free form or immobilized on support, while providing compounds of formula III having optical purity of 99 percent and above.

The II-to-III conversion is accomplished in a biphasic solvent system comprising an organic phase, immiscible in water, and an aqueous phase. Since the substrate (compound II) and product (compound III) are soluble in organic solvents, these compounds are contained in the organic phase of the biphasic solvent system. The water-soluble enzyme or enzymes used are contained within the aqueous phase. While the exact mechanism behind the present invention is not totally understood, it is believed that the two-phase solvent system enhances the efficiency of the present process. The data we have gathered (see Tables 1, 2 and 3) supports this conclusion.

Various enzymes, such as esterases, lipases and proteases, regardless of origin or purity, are suitable for use in the present invention. The enzyme or enzymes can be in the form of a mixture of animal and plant enzyme, cells of microorganisms, crushed cells or extracts of cells.

Typical genuses of microorganism suitable as sources of hydrolyzing enzymes include Mucor, Escherichia, Staphylococcus, Agrobacterium, Rhizopus, Aspergillus, Nocardia, Streptomyces, Trichoderma, Candida, Rhodotorula, Torulopsis. Bacillus, Alcaligenes, Pseudomonas, Brevibacterium, Enterobacter, Chromobacterium, Arthrobacter, Microbacterium, Mycobacterium, Saccharomyces, Penicillium, Botrytis, Chaetomium, Ophiobolus, Cladosporium and the like.

Commercially available enzymes suitable for use in the present invention include lipases, such as Amano AY-30 (*Candida cylindraces*), Amano P (*Pseudomonas fluorescens*), Amano N (*Rhizopus niveus*), Amano R (*Penicillium sp.*), Amano FAP (*Rhizopus oryzae*), Amano AP-12 (*Aspergillus niger*), Amano MAP (*Mucor meihei*), Amano GC-4 (*Geotrichum candidum*), Sigma L-0382 and L-3126 (porcine pancreas), Sigma L-3001 (Wheat germ), Sigma L-1754 (*Candida cylindracea*), Sigma L-0763 (*Chromobacterium viscosum*) and Amano K-30 (*Aspergillus niger*). Additionally, suitable enzymes derived from animal tissue include esterase from pig liver and α-chymotrypsin and pancreatin from pancreas.

Solvents for the organic phase of the biphasic solvent system can be any convenient organic solvent immiscible in water, such as toluene (which is preferred), cyclohexane, xylene, trichlorotrifluoroethane and the like.

The aqueous phase is conveniently of water, preferably deionized water or a suitable aqueous buffer solution (phosphate buffer preferred).

The biphasic solvent system may comprise between about 10 to 90 percent by volume of organic solvent and between about 90 to 10 percent by volume of aqueous solvent and is preferably at or about 20 percent by volume the organic phase and 80 percent by volume the aqueous phase.

A typical reaction system comprises a biphasic solvent system as described above, compound II in an amount from about 0.1 to about 100 mg/mL of biphasic solvent and one or more enzymes in an amount from about 0.1 to about 100 mg enzyme per mg of compound II to be hydrolyzed.

A typical embodiment of the present process starts with preparation of an aqueous solution of the enzymes to be used. For example, Pseudomonas lipase (which is preferred) can be added to a suitable amount of an aqueous solvent, such as phosphate buffer or the like. This mixture is preferably adjusted to and maintained at about pH 7.0, preferably with an aqueous alkali metal hydroxide, carbonate or bicarbonate. Centrifugation at reduced temperatures (e.g., 4° C.) provides the enzyme-containing aqueous portion of the biphasic solvent system.

Thereafter, an emulsion of compound II in an organic solvent (e.g., toluene) and aqueous solvent is formed and cooled. The enantioselective hydrolysis can be effectuated by adding the enzyme-containing aqueous solvent to this emulsion, preferably while continuing agitation and cooling. The reaction time may vary from enzyme to enzyme but typical reaction times are about 24 to 48 hours, depending on the enzyme concentration.

Thereafter, compound III wherein $R^1$ is typically methyl is oxidized to obtain the corresponding aldehydes IV or IV' or a mixture thereof, depending on oxidation and isolation conditions. Compounds IV and IV', either separately or as a mixture, are hydrolyzed by treatment with, for example, an alkali metal carbonate, bicarbonate and/or hydroxide (e.g., $K_2CO_3$, $KHCO_3$, KOH) and water to form compound V in nearly pure (−) enantiomeric form. During this base hydrolysis, compound IV' epimerizes optimally above pH 10 to the cis isomer IV or the corresponding alcohol, which cyclizes to form compound V. Intentional epimerization of compound IV provides a mixture of compounds IV and IV', which upon hydrolysis and cyclization provides only compound V.

Compound V is alkylated in a Wittig reaction (e.g., with $Ph_3P=CHOCH_3$ wherein Ph is phenyl), followed by aqueous acid treatment to form compound VI. Any of compounds I through VI may be conventionally hydrogenated to remove the double bond, if present.

Compound VI undergoes a Wittig reaction with
XII

wherein Ph is phenyl and M⊕ is an alkali metal ion (e.g., (4-carboxybutyl)triphenylphosphonium, potassium salt) at about −78° to 0° C. in tetrahydrofuran to form compound VII. For this Wittig reaction, M⊕ is preferred to be potassium ion. For purity, it is also preferred that oxygen be excluded by conducting the reaction in an inert atmosphere and by quenching with a nonaqueous acid. On a large scale, purity may be increased with the presence of a complexing agent such as 1,3-dimethyl-2-imidazolidinone, hexamethylphosphoramide (HMPA), or 1,3-dimethyl-3,4,5,6-tetrahydrofuran-2(1H)-pyrimidinone (DMPU).

Compound XII is derived preferably in situ by treating the known compound
XIII

wherein halo is preferably bromo with an alkali metal butoxide, amylate, hydride or disilazide (e.g., potassium t-butoxide, potassium t-amylate, potassium hydride, or potassium hexamethyldisilazide) in tetrahydrofuran. These procedures are described in copending U.S. patent application, "Process for Preparing a Cis Oxabicyclo Olefinic Acid and Ester from an Oxabicyclo Pyranol," filed on even date herewith, which is hereby incorporated by reference.

Compound VII is esterified with, for example, an ion-exchange resin (e.g., Amberlyst-15 ®) in an organic solvent (e.g., methanol) at about room temperature under an inert atmosphere (e.g., nitrogen) to form compound VIII wherein R is alkyl, aryl, cycloalkyl, aralkyl, or alkaryl, depending upon the solvent used in the esterification.

In a preferred alternative, compound VIII is prepared through an amine salt of the formula XIV

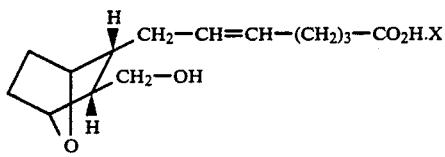

wherein X is an amine such as 1-adamantanamine, which is preferred. In this alternative process, compound XIV undergoes an acid-catalyzed esterification by treatment with an alcohol ROH (e.g., methanol, ethanol, isopropyl alcohol) in the presence of an organic or mineral acid (e.g., HCl) to form compound VIII. Compound XIV may be derived from compound VII by treatment with an amine such as 1-adamantanamine. Crystallization of compound XIV after such treatment helps to remove the undesired trans isomer. These procedures are also described in the copending U.S. patent application, "Process for Preparing a Cis Oxabicyclo Olefinic Acid and Ester from an Oxabicyclo Pyranol", filed on even date herewith, which is hereby incorporated by reference.

With the carboxyl group thus protected, the alcohol group may then be reacted. Compound VIII is reacted with an activating reagent (e.g., triphenylphosphine-diisopropylazodicarboxylate) in the presence of phthalimide in an organic solvent (e.g., dichloromethane, toluene, or tetrahydrofuran) at about 15° to 30° C. The resulting product is reacted with a strong base such as an alkali metal hydroxide, carbonate, or bicarbonate (e.g., NaOH) at about 0° to 100° C., optionally in the presence of an organic co-solvent such as tetrahydrofuran, to form compound IX.

Compound IX is then hydrolyzed with water and an aqueous acid (e.g., oxalic acid) in the presence of an organic co-solvent (e.g., tetrahydrofuran) with heating at reflux (25° to 70° C., with 60° to 65° C. preferred) to form compound X wherein A is a conjugate acid corresponding to the acid used in the hydrolysis. Mineral acids (e.g., HCl) or other organic acids (e.g., citric acid) may be employed in the hydrolysis to form compound X. Amino acid X is then acylated with [(1-oxoheptyl)amino]acetic acid at about 0° C. under an inert atmosphere (e.g., argon) in the presence of a coupling agent (e.g., 1,1-carbonyldiimidazole) and a tertiary amine base (e.g., N,N-diisopropylethylamine, tributylamine, or 1,8-diazabicyclo[5.4.0]undec-7-ene) to form compound XI.

Alternatively, to reduce the trans double bond contamination from the previous Wittig reaction, compound X may be first neutralized to compound X' by treatment with a base (e.g., triethylamine) in an organic solvent (e.g., methanol) with stirring at about 20 to 30° C. Neutralization could also be accomplished with an ion exchange resin or an inorganic base such as sodium or potassium hydroxide, carbonate, or bicarbonate. Like compound X, compound X' is finally acylated with [(1-oxoheptyl)amino]acetic acid to form compound XI.

The invention will now be further described by the following working examples, which are illustrative rather than limiting. These examples constitute preferred embodiments of the invention.

EXAMPLE 1

(−)-(exo,exo)-7-Oxabicyclo(2.2.1)heptane-2,3-dimethanol, monoacetate ester

1-A.

.(exo,exo)-7-Oxabicyclo[2.2.1]heptane-2,3-dimethanol

Lithium aluminum hydride pellets (about 27.3 g were added portionwise to a solution of tetrahydrofuran (about 1 L) under argon. After stirring for 0.5 hr, (3aα,4β,7β,7aα)hexahydro-4,7-epoxy-isobenzofuran-1(3H)-one (50.0 g) was added portionwise and at such a rate as to maintain the internal temperature around 40° C. The suspension was then stirred at ambient temperature for 22 hours.

The reaction was quenched by the slow dropwise addition of H$_2$O (32 mL), 15% NaOH (32 mL), and H$_2$O (90 mL). After stirring for one hour, the white precipitate was filtered, and the solids washed with tetrahydrofuran (2×50 mL). The combined filtrates were dried (MgSO$_4$), filtered, and concentrated to a yellow oil that solidified on standing. Ether (50 mL) was added and the mixture was allowed to stand at 0° C. for 16 hours. After filtration, the solids were triturated with hexanes. Filtration and drying then afforded 50.8 g (99%) of diol 1-A.

1-B.

(exo,exo)-7-Oxabicyclo[2.2.1]heptane-2,3-dimethanol, diacetate ester

Acetic anhydride (50 mL) was added to a solution of diol 1-A (16.9 g) in pyridine (100 mL). The internal temperature increased to approximately 30° C. The reaction was then left at room temperature for 20 hours.

The solution was concentrated and then co-evaporated several times with toluene/methanol to remove the acetic anhydride and pyridine. Ethyl acetate (250 mL) was added and the solution extracted with 0.5% aqueous HCl (1×50 mL), H$_2$O (1×50 mL), saturated aqueous NaHCO$_3$ (2×50 mL), and saturated brine (3×50 mL). The organic phase was dried (MgSO$_4$), filtered, and concentrated to a solid. Trituration with hexanes and filtration afforded diacetate 1-B (23.3 g, 90% yield) as a white crystalline solid.

1-C. (−)-(exo,exo)-7-Oxabicyclo(2.2.1) heptane-2,3-dimethanol, monoacetate ester An enzyme solution was prepared by mixing 4 g (120,000 units) of crude Pseudomonas lipase P-30 (Amano International, USA) in 200 mL of 50 mM phosphate buffer, pH 7.0. The pH was checked and adjusted to 7.0 with 2 N sodium hydroxide. The suspension was centrifuged at 10,000 RPM for 15 minutes at 4° C. to remove insoluble materials. The recovered supernatant was cooled to 4° C., to be ready for use below.

To 50 mM phosphate buffer (600 mL, pH 7.0) was added toluene (200 mL) containing 2 g of diester 1-B. The so-formed emulsion of toluene in buffer was then cooled to and maintained at 5° C. The 200 mL of 50 mM phosphate buffer, pH 7.0 containing 5 g (150,000 units) of the crude Pseudomonas P-30 lipase was then introduced to the solution while continuing the agitation at 200 RPM. The reaction was allowed to continue for 47 hours and the pH was maintained at 7.0 by the addition, as necessary, of 2.5 N sodium hydroxide using a pH stat. During reaction, at various time intervals, 5 mL samples were taken, extracted with 5 volumes of ethyl acetate (25 mL). The ethyl acetate layers were separated and evaporated to dryness to obtain an oily residue containing the title compound. The amount of substrate 1-B and product Example 1 was analyzed by gas chromatography. The optical purity of the product was determined by chiral HPLC.

After completion of the hydrolysis (47 hours), the reaction mixture was extracted with 5 volumes of ethyl acetate (5 liters) and the ethyl acetate layer was separated from aqueous layer. The ethyl acetate layer was evaporated under vacuum to yield 1.3 grams of the title compound with an (−) enantiomeric purity of 96.8% (Table 1).

EXAMPLES 2 TO 6

The procedures of Example 1 were repeated in these examples, except that part C was carried out under the parameters defined below. The results are summarized in Table 1, the product in each case being (−)-(exo,exo)-7-oxabicyclo(2.2.1)heptane-2, 3-dimethanol, monoacetate ester.

EXAMPLE 2

Enzyme: Pseudomonas lipase (Biocatalyst, UK)
Biphasic solvent: 4 mL toluene, 36 mL of 50 mM phosphate buffer, pH 7.0
Sustrate: 2 mg compound 1-B/mL biphasic solvent
Enzyme per substrate: 10 mg/mg of substrate
Temperature: 4° C.

EXAMPLE 3

Enzyme: Pseudomonas lipase (Enzymatics, UK)
Biphasic solvent: 4 mL toluene, 36 mL of 50 mM phosphate buffer, pH 7.0
Substrate: 2 mg compound 1-B/mL biphasic solvent
Enzyme per substrate: 10 mg/mg of substrate
Temperature: 4° C.

EXAMPLE 4

Enzyme: Pseudomonas lipase (Amano International, USA)
Biphasic solvent: 4 mL toluene, 36 mL of 50 mM phosphate buffer, pH 7.0
Substrate: 2 mg compound 1-B/mL biphasic solvent
Enzyme per substrate: 10 mg/mg of substrate
Temperature: 4° C.

EXAMPLE 5

Enzyme: Pseudomonas lipase (Squibb, USA)
Biphasic solvent: 8 mL toluene, 32 mL of 50 mM phosphate buffer, pH 7.0
Substrate: 2 mg compound 1-B/mL biphasic solvent
Enzyme per substrate: 10 mg/mg of substrate
Temperature: 4° C.

EXAMPLE 6

Enzyme: Porcine pancreatic lipase (Sigma Chemicals, USA)
Biphasic solvent: 8 mL toluene, 32 mL of 50 mM phosphate buffer, pH 7.0
Substrate: 2 mg compound 1-B/mL biphasic solvent
Enzyme per substrate: 10 mg/mg of substrate
Temperature: 4° C.

EXAMPLE 7

(−)-(exo,exo)-7-Oxabicyclo(2.2.1)heptane-2,3-dimethanol, monoacetate ester

A. Crude Pseudomonas lipase P-30 (500 g) was dissolved in 2600 mL of deionized water and centrifuged at 12,000 RPM for 20 minutes to remove insoluble materials. The clear supernatant solution was added to 50 grams of Accurel polypropylene (Enka Industrial Products, Co., USA) which was previously washed with methanol. The enzyme and carrier (Accurel Polypropylene) slurry was incubated at 28° C. for 24 hours at 150 RPM on a shaker. Immobilized lipase on Accurel polypropylene was filtered and washed with water. The resins were then dried under vacuum at 25° C. for 24 hours. About 56 grams of immobilized lipase on Accurel polypropylene was obtained.

Reaction was conducted in a 5-liter jacketed reactor. The reactor contained 2.7 liters of 50 mM phosphate buffer, pH 7.0 containing 7.5 grams of Pseudomonas lipase P-30 (Amano International, USA) immobilized on Accurel polypropylene as described above. The reaction was started by addition of 300 mL of toluene containing 15 g of substrate 1-B. The reaction was carried out at 5° C., 200 RPM agitation, and pH 7.0 (maintained by 5.25 N NaOH with a pH stat). Based upon analysis by gas chromatography, 89 M % conversion of substrate 1-B to product 1-C was achieved after 26 hours (Table 2).

B. Another 3-liter batch was conducted following the above procedures. After 27.5 hours of hydrolysis, 82 M % conversion of substrate diacetate ester to product (−)monoacetate ester was obtained. Both batches, containing a total 6-liter reaction mixture, were used for recovery and crystallization of (−)-(exo,exo)-7-oxabicyclo (2.2.1)heptane-2,3- dimethanol monoacetate ester as follows.

The above-named monoacetate ester product from the 6-liter reaction was extracted with 30 liters of ethyl acetate. The ethyl acetate extract was separated and concentrated to obtain 27 grams of oily materials. The concentrates were placed at 7° C. overnight, and the oily solids were washed with hexane (3×100 mL). The solids were then dissolved in 100 mL of methylene chloride, with subsequent addition of 100 mL of hexane. Crude crystals were formed upon the concentration of the solution under reduced pressure. The crude crystals were separated from the mother liquor and recrystallized in a 1:1 methylene chloride and hexane mixture to yield white crystals (14 g) with a 99.5% optical purity (chiral HPLC and NMR analysis). Gas chromatography of the preparation gave 99.5% HI. Thin layer chromatography (Rf=0.46, ethyl acetate:hexane, 70:30, v/v), melting point 80.5° C.

EXAMPLES 8 TO 14

The procedures of Example 7 were followed in these examples under the parameters defined below. The results for Examples 7 to 13 are summarized in Table 2, the product in each example being (−)-(exo,exo)-7-oxabicyclo(2.2.1) heptane-2,3-dimethanol, monoacetate ester.

EXAMPLE 8

Enzyme: Immobilized Pseudomonas lipase on Accurel-pp (Enzymatics, UK)
Biphasic solvent: 4 mL toluene, 36 mL of 50 mM phosphate buffer, pH 7.0
Substrate: 2 mg compound 1-B/mL biphasic solvent
Enzyme per substrate: 0.5 mg of immobilized enzyme/mg of substrate
Temperature: 4° C.

EXAMPLE 9

Enzyme: Immobilized Pseudomonas lipase on Accurel-pp (Biocatalyst, UK)
Biphasic solvent: 4 mL toluene, 36 mL of 50 mM phosphate buffer, pH 7.0
Substrate: 2 mg compound 1-B/mL biphasic solvent
Enzyme per substrate: 0.5 mg of immobilized enzyme/mg of substrate
Temperature: 4° C.

EXAMPLE 10

Enzyme: Immobilized Pseudomonas lipase on Accurel-pp (Amano International, Co. USA)
Biphasic solvent: 4 mL xylene, 36 mL of 50 mM phosphate buffer, pH 7.0
Substrate: 2 mg compound 1-B/mL biphasic solvent
Enzyme per substrate: 0.5 mg of immobilized enzyme/mg of substrate
Temperature: 4° C.

EXAMPLE 11

Enzyme: Immobilized Pseudomonas lipase on Accurel-pp (Amano International, Co. USA)
Biphasic solvent: 8 mL toluene, 32 mL of 50 mM phosphate buffer, pH 7.0
Substrate: 2 mg compound 1-B/mL biphasic solvent
Enzyme per substrate: 0.5 mg of immobilized lipase/mg of substrate
Temperature: 4° C.

EXAMPLE 12

Enzyme Immobilized Pseudomonas lipase on Accurel-pp (Amano International, Co. USA)
Biphasic solvent: 8 mL trichlorotrifluoroethane, 32 mL of 50 mM phosphate buffer, pH 7.0
Substrate: 2 mg compound 1-B/mL biphasic solvent
Enzyme per substrate: 0.5 mg of immobilized lipase/mg of substrate
Temperature: 25° C.

EXAMPLE 13

Enzyme: Immobilized Pseudomonas lipase on Accurel-pp (Amano International, Co. USA)
Aqueous solvent: 40 mL of 50 mM phosphate buffer, pH 7.0
Substrate: 2 mg compound 1-B/mL aqueous solvent
Enzyme per substrate: 0.5 mg of immobilized lipase/mg of substrate
Temperature: 4° C.
(Example 13 is present to demonstrate the advantages of the biphasic system—see Table 2.)

EXAMPLE 14

Enzyme: Immobilized Pseudomonas lipase (Amano P-30) on Accurel-pp bead (200 g)
Biphasic solvent: 8 L toluene, 72 L of 0.05 M potassium phosphate solution
Substrate: 400 g compound 1-B
Temperature: 5±0.5° C.

EXAMPLE 15

[3aR-(3aα,4β,7β,7aα)]-Octahydro-4,7-epoxy-isobenzofuran-1-ol

15-A.

1S-(1α,2α,3α,4α)]-3-[(Acetyloxy)methyl-7-oxabicyclo[2.2.1]heptane-2-carboxaldehyde A solution of oxalyl chloride (3.8 mL, 43.56 mmol) in dichloromethane (125 mL) was cooled to −60° C. under argon. A solution of dimethylsulfoxide (8.0 mL, 112.7 mmol) in dichloromethane (20 mL) was added dropwise over 15 minutes while maintaining the internal temperature at −60° C. The solution was stirred another 15 minutes at −60° C.

A solution of compound 1-C (5.1 g, 25.28 mmol, 99.3% optical purity by chiral shift NMR) in dichloromethane (20 mL) was added dropwise over 10 minutes at −60° C. The resulting cloudy mixture was stirred another 20 minutes at −60° C. Diisopropylethylamine (37 mL, 212.41 mmol) was added dropwise over 25 minutes at −60° C. The resulting clear solution was warmed to −45° C. and stirred until no starting material was left by TLC (about 35 additional minutes).

The reaction was quenched by the addition of 125 mL of 10% HCl to the solution. After the solution froze, the cooling bath was removed and the mixture was stirred until completely melted and then for an additional 45 minutes.

The solution was transferred to a separatory funnel and the layers were separated. The aqueous phase was extracted with dichloromethane (2×50 mL). The combined organic layers were washed with 10% HCl (2×100 mL), water (1×50 mL), saturated NaHCO₃ (1×75 mL), and saturated NaCl (2×100 mL). The organic layer was dried over magnesium sulfate, then filtered and concentrated in vacuo to 5.45 g of a crude yellow solid (110%). The crude product was stirred in hexane, filtered and dried in vacuo to produce 5.1 g of cis-aldehyde 15-A (96%), melting point 39.0°–41.5° C.

15-B.

[3aR-(3aα,4β,7β,7aα)]-Octahydro-4,7-epoxyisobenzofuran-1-ol

Solid potassium carbonate was added to a room temperature suspension of aldehyde 15-A (3.654 g, 18.45 mmol) in water (30 mL) to adjust the pH to 11. The solution was maintained at pH 10.95 to 11.10 with additions of 40% KOH (w/v) until the hydrolysis was complete by TLC.

The solution was neutralized with glacial acetic acid added in small portions to control foaming. Solid NaCl was added and stirred in order to saturate the solution. The solution was filtered to remove excess solid NaCl. The solution was extracted with 10% acetonitrile in ethyl acetate (15×20 mL). The organic layers were combined, dried over magnesium sulfate, filtered, and concentrated in vacuo to 2.65 g (95%) of crude yellow solid.

A portion of the crude product (0.98 g) was purified by dissolving it in 1 mL of dichloromethane, followed by the addition of cold cyclohexane (4×1 mL) with stirring. Upon addition of the fourth milliliter of cyclohexane, the product immediately crystallized. After refrigeration overnight, the solid was filtered, washed with hexane, and dried in vacuo to give 0.65 g (66%) of Example 15.

EXAMPLE 16

(3aα,4β,7β,7aα)-Octahydro-4,7-epoxy-isobenzofuran-1-ol

16-A. (±)-(exo,exo)-7-Oxabicyclo(2.2.1)heptane-2,3-dimethanol, monoacetate ester Sodium hydride (835 mg, 20.9 mmol) was added portionwise to a solution of compound 1-A (3.0 g, 19.0 mmol) in tetrahydrofuran (100 mL) at room temperature. After stirring for 4 hours, the mixture was cooled to −10° C. and acetyl chloride (1.55 mL, 21.9 mmol) was added. The reaction was then allowed to warm to ambient temperature and stirred for an additional 16 hours. Acetic acid (0.25 mL) was added, followed by Celite (2 g). The suspension was then filtered through Celite with the residual solids being washed with additional tetrahydrofuran. The combined filtrates were concentrated to a semi-solid and applied to a silica gel column. Elution using ether-hexanes (1:1) afforded the monoacetate 16-A (2.32 g, 61% yield) as a clear colorless oil that slowly crystallized on standing.

16-B. (±)-(1α,2α,3α,4α)-3-[(Acetyloxy)methyl]-7-oxabicyclo[2.2.1]heptane-2-carboxaldehyde A solution of oxalyl chloride (60 mL) in dichloromethane (2000 mL) was cooled to −60° C. and was treated with stirring over 15 minutes with a solution of dimethylsulfoxide (124 mL) in dichloromethane (300 mL). The solution was stirred for 15 minutes at −60° C.

A solution of compound 16-A (80 g) in dichloromethane (500 mL) was added over 10 minutes and the reaction was stirred for an additional 30 minutes. Diisopropylethyl amine (600 mL) was added over five minutes at −60° C. Cooling was removed and the temperature rose to 45° C. over 10 minutes. The cold mixture was added to 2000 mL of ice water under stirring.

The organic layer was separated and the aqueous layer was extracted two times with 500 mL dichloromethane. The combined organic layers were extracted with 10% hydrochloric acid (1400 mL), water (600 mL), saturated sodium hydrogen carbonate (1200 mL) and brine (1000 mL). The organic phase was dried over magnesium sulfate, filtered and concentrated to a syrup which solidified on standing. The solids were broken up, stirred with 50 mL hexane, filtered and dried to give compound 16-B, 78.5 g (99%) corrected for water, melting point 43°-44° C., with about 30% trans isomer IV' ($R^1$=CH$_3$).

TLC: Ethyl acetate, $R_f$ 0.5, visualization ammonium molybdate/ceric sulfate.

The foregoing procedure may be used with the monoacetate ester prepared as described in Examples 1 to 14 to reduce the trans isomer contamination.

16-C. (±)-(3aα,4β,7β,7aα)-Octahydro-4,7-epoxyisobenzofuran-1-ol

The product from 16-B above (80 g) was dissolved in 392 mL water. A small amount of solids remained undissolved. The mixture was treated with 70 mL hexanes, was stirred, filtered and the layers were separated. The pH was 2.32. The aqueous layer was treated dropwise under nitrogen with 50% sodium hydroxide to maintain pH 10.8 to 11.0. 20.9 mL were added over 6 hours.

The pH 11.0 solution was neutralized to pH 7.0 with 1.6 mL glacial acetic acid and was saturated with solid sodium chloride. After stirring for 15 minutes, the aqueous solution was extracted with 10% acetonitrile in ethyl acetate (12×350 mL). The combined organic extracts were dried over magnesium sulfate and then were concentrated to dryness. A soft crystalline solid was obtained. The solids were triturated with 75 mL ethyl ether, filtered and dried. 54 g of compound 16-C were obtained, 85.5% yield, melting point 123°–124° C.

EXAMPLE 17

[1S-[1α,2α(Z),3α,4α]]-7-[3-[[[[(1-oxoheptyl)amino]-acetyl]amino]methyl-7-oxabicyclo[2.2.1]hept-2-yl]-5-heptenoic acid

17-A. [4aR-(4aα,5β,8β,8aα)]-Octahydro-5,8-epoxy-1H-2-benzopyran-3-ol

A slurry of methoxymethyltriphenylphosphonium chloride (1.09 kg, 3.18 mol) in Burdick and Jackson sieve-dried tetrahydrofuran (3 liters) was chilled to 0° C. and treated dropwise with 1.4 M potassium t-amylate in toluene (1910 mL, 2.67 mol) over twenty minutes. The resultant dark red solution was stirred at 0° C. for one hour. The mixture was then treated slowly over five minutes with solid compound V or Example 15 (200 g, 1.28 mol). The temperature gradually rose to 23° C. The mixture was stirred vigorously at room temperature for ninety minutes. The reaction mixture was then chilled to 0° C. and treated slowly with acetaldehyde (124 mL, 2.2 mol) over ten minutes. The mixture was diluted with water (2500 mL) and treated with 10% hydrochloric acid to pH 7. The mixture was then extracted with ether (7×2 liters). The combined ether extracts were dried over magnesium sulfate, filtered, and the filtrates concentrated in vacuo. The resultant mixture was treated with isopropyl ether (4 liters) and stirred overnight. The mixture was chilled to −10° C. for ninety minutes and then filtered. The solids were washed thoroughly with isopropyl ether. The filtrate was concentrated in vacuo to an oily residue (460 g). This oily residue was treated with water (4000 mL) and stirred vigorously for two hours. The aqueous layer was decanted and the oily residue treated two additional times with water (2×1 liter). After the third wash, the residue solidified and was filtered. The combined aqueous triturates were concentrated in vacuo to 3.5 liters. The cloudy mixture was filtered through a bed of Celite. The filtrate was concentrated again to a volume of 2.3 liters. The cloudy solution was chilled in an ice bath and treated slowly with concentrated hydrochloric acid (683 mL). The mixture was then stirred at room temperature for three hours. After this time the solution was neutralized by the slow addition of solid sodium bicarbonate (720 g). The mixture was filtered through a bed of Celite and extracted first with hexane (4×2 liters), then with ethyl acetate (10×2 liters). The combined ethyl acetate extracts were dried over MgSO$_4$ and concentrated in vacuo. The solid residue was triturated with hexane (1 liter), filtered and dried in vacuo to yield 220 g (100%) of desired compound 17-A.

Melting point 104°–105° C., $[\alpha]_D = +27°$ c = 1, methanol.

TLC: Silica gel; ethyl acetate; $R_f = 0.3$; $Ce(SO_4)_2$.

17-B.
[1S-[1α,2α(Z),3α,4α]]-7-[3-(Hydroxymethyl)-7-oxabicyclo[2.2.1]hept-2-yl]-5-heptenoic acid A slurry of 4-carboxybutyltriphenylphosphonium bromide (665 g, 1.47 mol) and compound 17-A (170 g, 1 mol) in Burdick and Jackson sievedried toluene (4 liters) was chilled to 0° C. and treated dropwise with a solution of 1.39 M potassium t-amylate in toluene (2060 mL, 2.86 mol) over ninety minutes. The mixture was then stirred at room temperature for twenty hours. The mixture was chilled at 5° C. and treated slowly with glacial acetic acid (161 mL, 2.83 mol) in toluene (200 mL) over thirty minutes. The thick suspension was treated with water (3 liters), then concentrated with hydrochloric acid (236 mL) to pH 2.6. The reaction mixture was diluted with ethyl acetate (3 liters), treated with sodium chloride (700 g), seeded with starting phosphonium salt and stirred vigorously for fifteen minutes. The resultant precipitate was then removed by filtration and washed with ethyl acetate (2×1500 mL). The toluene-ethyl acetate layer was separated and the aqueous layer extracted with ethyl acetate (2×1500 mL). The combined ethyl acetate extracts were dried over magnesium sulfate and concentrated in vacuo to a thick oil. The oil was stirred vigorously with 5% potassium carbonate (3000 mL) for thirty minutes. The resultant solid was filtered and washed thoroughly with water. The aqueous filtrate was extracted with 50/50 ether/toluene (5×1 liter). The aqueous layer was then chilled in an ice bath and treated slowly with concentrated hydrochloric acid to pH 2.5. The aqueous layer was extracted with ethyl acetate (1×2 liters, 2×1 liter). The combined extracts were dried over magnesium sulfate and concentrated in vacuo. The resultant oil was azeotroped twice with toluene to yield 241 g of solid. This solid was triturated with cold ether (1 liter) and filtered to yield 220 g of desired alcohol acid 17-B.

TLC: Silica gel; ethyl acetate/acetic acid (20:1); $R_f = 0.5$; $Ce(SO_4)_2$.

17-C.
[1S-[1α,2α(5Z),3α,4α]]-7-[3-(hydroxymethyl)-7-oxabicyclo[2.2.1]hept-2-yl]-5-heptenoic acid, methyl ester A solution of compound 17-B (353 g, 1.38 mol) in methanol (1800 mL) was treated with crushed Amberlyst-15 resin (180 g), then stirred vigorously at room temperature for two days. The reaction mixture was diluted with diethyl ether (1800 mL) and filtered through Celite. The pad was washed thoroughly with ether and the combined filtrates concentrated in vacuo. The resultant oil was dissolved in ether (3 liters) and washed with 5% sodium bicarbonate, water (500 mL) and brine (500 mL), then dried over magnesium sulfate and concentrated in vacuo to a thick oil that solidified when chilled over a prolonged period of time.

Yield: 370 g.

TLC: Silica gel; ether; $R_f = 0.4$; $Ce(SO_4)_2$.

17-D.
[1S-[1α,2α(Z),3α,4α]]-7-[(3-(Aminomethyl)-oxabicyclo[2.2.1]hept-2-yl]-5-heptenoic acid, oxalate (1:1) salt A dry 500-mL flask equipped with stirrer, argon (nitrogen) inlet, thermometer and dropping funnel was charged with [1S[1α,2α(Z),3α,4α]]-7-[ 3-hydroxymethyl)-7-oxabicyclo[2.2.1]hept-2-yl]-5-heptenoic acid, methyl ester (20.007 g, 74.65 mmol, triphenylphosphine (22.518 g, 85.85 mmol) and dichloromethane (270 mL from a freshly or recently opened bottle). After stirring several minutes to obtain a clear solution, finely ground phthalimide (12.082 g, 82.12 mmol) was added. While maintaining the internal temperature at about 20° to 25° C. with a water bath, a solution of diisopropylazodicarboxylate (16.907 g, 93.61 mmol) in dichloromethane (45 mL) was added dropwise over 30 minutes. After the addition, the reaction was stirred at room temperature for 4 hours.

The solvent was removed in vacuo to a heavy oil which was dissolved in toluene (450 mL). The resulting solution was washed with ice cold 0.25 M NaOH (3×80 mL), cold water (1×80 mL) and brine (1×80 mL). The toluene solution was dried over sodium sulfate, filtered and concentrated to a heavy oil, which was dissolved in tetrahydrofuran (350 mL) and treated (under argon) via a dropping funnel with a solution of lithium hydroxide monohydrate (10.964 g, 261.29 mmol) in 260 mL of distilled water. The reaction was vigorously stirred under argon for 2 hours and acidified to pH 9.6 with about 20 mL of concentrated hydrochloric acid (added dropwise over about 15 minutes).

The reaction was transferred to an evaporating flask and 331 mL of solvent was removed in vacuo at ≦30° C. Ethyl acetate (250 mL) was immediately added to the residue and the mixture was transferred to a separatory funnel and shaken. The organic layer was discarded and the aqueous layer was washed with additional ethyl acetate (3×250 mL).

The product-rich aqueous layer was stirred while adjusting the pH from 8.8 to 7 with several drops of concentrated hydrochloric acid. Ethyl acetate (400 mL) was added and the resulting two-phase system was vigorously stirred while lowering the pH of the aqueous layer to two.

After transferring to a separatory funnel and separating the layers, the aqueous layer was washed with additional ethyl acetate (2×100 mL). The combined product-rich organic layers were washed with half-saturated brine (1×240 mL) and brine (1×200 mL) and dried over sodium sulfate. The organic solution was filtered and concentrated in vacuo at ≦30° C. The resulting solid phthalamic acid derivative was dried under high vacuum to 29.17 g.

The phthalamic acid was dissolved in tetrahydrofuran (150 mL) and evaporated to remove traces of ethyl acetate. The material was dissolved in tetrahydrofuran (243 mL including the amount left after the evaporation) and added to a 500-mL flask equipped with mechanical stirrer and argon inlet. Anhydrous oxalic acid (13.437 g, 149 mmol) was added followed by water (68 mL). The resulting hazy solution was stirred at a gentle reflux under argon for 6.5 hours. Heating was discontinued and the mixture stirred overnight.

The resulting crystal slurry was stirred while cooling at 0° C. for 4 hours. The product was filtered and washed with tetrahydrofuran (2×140 mL), ethyl acetate (3×140 mL), and hexane (3×140 mL). The title compound was dried under high vacuum, initially at room temperature to a constant weight of 18.899 g, and then at 50° C. overnight to 18.880 g.

Melting point: 184°–187° C.

17-E.
[1S-[1α,2α(Z),3α,4α]]-7-[(3-Aminomethyl)-7-oxabicyclo[2.2.1]hept-2-yl]-5-heptenoic acid

Method I

A suspension of [1S-1α,2α(Z),3α,4α]-7-[(3-aminomethyl)-7-oxabicyclo[2 2.1]hept-2-yl]-5-heptenoic acid, oxalate (1:1) salt (6.72 g corrected weight, 19.568 mmol; containing 2.25% trans olefin by HPLC) in methanol (70 mL) was stirred under argon and treated over 5 minutes with triethylamine (6.73 mL, 41.1 mmol). An additional 6 mL of methanol was added and the heavy slurry was stirred at room temperature overnight. The slurry was filtered and the crude product was washed with methanol, ether, and hexane and dried in vacuo to 3.55 g (72%) of the title compound containing 0.64% trans olefin by HPLC.

A portion of the product (3.0 g) was slurried in methanol-water (18 mL–4.5 mL) and stirred overnight. The slurry was filtered and washed with 15% aqueous methanol, methanol, ether and hexane. After drying in vacuo the product weighed 2.224 g and contained ≦0.05% olefin by HPLC.

Melting Point: 223°–235° C. with decomposition.

The mother liquors from a large scale run (606 g input of oxalate salt) were combined and concentrated in vacuo using toluene to remove water. The residue was slurried in methanol (3 L), stirred overnight and filtered to afford 294 g of [1S-[1α,2α(Z),3α,4α]]-7-[(3-aminomethyl)-7-oxabicyclo-[2.2.1]hept-2-yl-5-heptenoic acid, hemioxalate salt. This material was slurried in methanol (2200 mL), treated with triethylamine (100.32 g) and stirred at room temperature overnight. The slurry was filtered and washed with methanol and ether to afford 217 g of the title compound.

Method II

A 3-necked flask equipped with overhead stirrer and reflux condenser was charged with [1S-[1α,2α(Z),3α,4α]]-7-[(3-aminomethyl)-7-oxabicyclo[2.2.1]hept-2-yl]-5-heptenoic acid, 1:1 oxalate salt (10 g, 28.29 mmol after correction for residual water; 3.7% trans double bond isomer by HPLC), methanol (60 mL), and water (8 mL). The mixture was cooled in an ice bath and treated with triethylamine (8.3 mL, 59.41 mmol). The cooling bath was removed and the slurry was stirred at ambient temperature for 20 minutes and then heated to reflux. Water was added slowly via the condenser until a clear solution was obtained (12 to 13 mL required). An additional 1 mL of water was then added, and the mixture was cooled while stirring and seeded at a bath temperature of 40° C. Stirring was continued at ambient temperature overnight, and then at 0° C. for several hours.

The product was filtered and washed with 5% aqueous methanol (3×10 mL), methanol (3×20 mL), ether (3×25 mL), and hexane (3×25 mL). The yield of the title compound was 4.84 g (68%). HPLC indicated the presence of 0.5% trans double bond isomer.

Melting point: 234°–235° C. with decomposition.

A slurry of 1 g of this product in 6 mL of methanol was treated with 2.5 mL of water. The resulting slurry was stirred at room temperature overnight and filtered. The product was washed with 70% methanol-water, methanol, ether, and hexane. The recovery of the title compound was 656 mg. HPLC analysis indicated ≦0.05% trans double bond isomer.

17-F.
[1S-[1α,2α(Z),3α,4α]]-7-[3-[[[[(1-Oxoheptyl)amino]acetyl]amino]methyl]-7-oxabicyclo[2.2.1]hept-2-yl]-5-heptenoic acid

Method I

A suspension of [(1-oxoheptyl)amino]acetic acid (2.673 g, 14.273 mmol) in dichloromethane (80 mL) was stirred under argon at 0° C. and treated with solid 1,1-carbonyldiimidazole (CDI; 22.5 g, 13.873 mmol) over 3 minutes. The resulting suspension was stirred briefly at 0° C. and then at room temperature for 2.5 hours. The resulting solution was cooled to 0° C. and treated with solid [1S-[1α,2α(Z),3α,4α]]-7-[3-aminomethyl)-7-oxabicyclo[2.2.1]hept-2-yl]-5-heptenoic acid, oxalate (1:1) salt (4.7 g, 13.339 mmol) followed by N,N-diisopropylethylamine (7.09 mL, 40.685 mmol). The reaction was stirred vigorously for 4 hours and treated with 1 N HCl (40 mL). Additional HCl was then added to lower the pH of the aqueous layer to 2.5. The biphasic mixture was transferred to a separatory funnel, the layers were separated and the aqueous layer was extracted with dichloromethane (3×10 mL). The three organic extracts were added to the original dichloromethane layer and the resulting organic solution was washed with 1 N HCl (3×50 mL), water (3×40 mL), and brine 1×50 mL).

The organic solution was concentrated in vacuo to a small volume, and ethyl acetate was added and evaporated. The resulting solid was recrystallized from ethyl acetate. The product was filtered, washed with ethyl acetate and hexane and dried in vacuo. The yield of the title compound was 4.895 g (86%).

Melting point: 117° to 119° C.

Method II

A suspension of [(1-oxoheptyl)amino]acetic acid (102.75 g, 0.55 mol) in dichloromethane (2600 mL) was chilled to 0° C. under a gentle sweep of argon and treated with carbonyldiimidazole (CDI) (85.16 g, 0.525 mol) in one portion. The reaction mixture was stirred at 0° C. for about five minutes then warmed to 25° C. over fifteen minutes. The reaction was then stirred at 25° C. (internal temperature maintained with a warm water bath) for three hours. The resultant solution was chilled at 0° C., treated with diisopropylethylamine (85.67 g, 0.66 mol), stirred for about five minutes, then treated with powdered [1S-[1α,2α(Z),3α,4α]]-7-[ (3-aminoethyl)-7-oxabicyclo[2.2.1]hept-2-yl]-5-heptenoic acid, (129.7 g, 0.51 mol with residual water correction). The reaction slurry was stirred at 0° to 2° C. for five hours.

The slurry was treated with 1800 mL of 1 N HCl in one portion (exotherm to 22° C.), stirred for about five minutes, then the layers were separated. The acidic aqueous layer (pH 2.1) was extracted with dichloromethane (3×400 mL). The combined organic layers were washed with 1 N HCl (3×2 liter) and water (3×2 liter). Each aqueous was extracted with dichloromethane (200 mL) and added to the main extract before each subsequent wash. The organic layer was dried over magnesium sulfate, filtered, and concentrated in vacuo to a dry solid (220 g).

The residue was combined with ethyl acetate (2550 mL) and heated until dissolution, then left standing at room temperature overnight. The resultant solid was filtered and the solid washed sequentially on the frit with ethyl acetate (3×600 mL) and hexane (3×600 mL) to yield 170 g of the title compound.

Melting point: 116°-118° C. [a]$_D$=7.1° (c=1,methanol).

EXAMPLE 18

[1S-[1α,2α(Z),3α,4α]]-7-[3[[[(1-oxoheptyl-)amino]acetyl]amino]methyl-7-oxabicyclo[2.2.1]hept-2-yl]-5-heptenoic acid The procedures of Example 17 were followed, except that compounds 17-B and 17-C were prepared as described below.

Method I

18-A.

[1R-[1α,2α(Z),3α,4α]]-7-[3-(Hydroxymethyl)-7-oxabicyclo[2.2.1]hept-2-yl]-5-heptenoic acid, 1-adamantanamine (1:1) salt A 500-mL, 3-necked flask equipped with argon inlet, thermometer and overhead stirrer was charged with 150 mL of a 1 M tetrahydrofuran solution of potassium tert-butoxide (Aldrich) and cooled to an internal temperature of −2° C. (4-Carboxybutyl)triphenylphosphonium bromide (32.867 g, 74.14 mmol; dried in vacuo at 100° C. overnight) was added in portions over 15 minutes while maintaining an internal temperature of 0°-5° C. The resulting orange-red mixture was stirred at 0° C. for an additional 15 minutes and then at ambient temperature for 2 hours. The red mixture was then cooled to −72° C. and treated, via cannula, over 15 minutes with a chilled (−30° C.) solution of R-enantiomer 17-A (5.862 g, 34.48 mmol) in 55 mL of distilled tetrahydrofuran. The reaction was allowed to stir while warming slowly (cooling bath in place) to room temperature. Solid lithium bromide (6 g, 68.96 mmol) was added, the reaction was stirred an additional 1.5 hours and cooled to 0° C. While maintaining the internal temperature at ≦10° C., 50 mL of 3 M hydrochloric acid was added. The mixture was further diluted with 100 mL of water followed by 150 mL of ethyl acetate.

After transferring to a separatory funnel, the layers were separated and the aqueous layer extracted with additional ethyl acetate (3×70 mL). The combined organic extracts were washed with 60 mL of 1 M hydrochloric acid, 60 mL of water and then with saturated sodium bicarbonate solution (2×150 mL, 3×5 mL). The product-rich basic extracts were washed with ethyl acetate (2×100 mL) and acidified to pH 2 with concentrated hydrochloric acid. The acidic mixture was extracted with dichloromethane (2×150 mL, 2×50 mL). The organic extracts were washed with brine, dried over sodium sulfate and filtered. The filtrate was concentrated in vacuo to an orange oil that was evaporated from ethyl acetate (2×100 mL) to a very heavy slurry (22.5 g). Additional ethyl acetate (97 mL) was added and the mixture was heated to dissolve suspended material. The resulting slurry was cooled to room temperature and stirred overnight. 5-(Diphenylphosphinyl)pentanoic acid was removed by filtration and washed with ethyl acetate. The filtrate was concentrated in vacuo to 9.611 g of crude [1R-[1α,2α(Z),3α,4α]]-7-[3-(hydroxymethyl)-7-oxabicyclo[2.2.1]hept-2-yl]-5-heptenoic acid.

A 3-necked 1-L flask equipped with overhead stirrer, and reflux condenser capped with nitrogen inlet was charged with a solution of the above crude product in warm ethyl acetate (185 mL). A solution of 1-adamantanamine was prepared separately by slurrying 6.98 g (46.05 mmol) in 150 mL of ethyl acetate followed by filtration, concentration in vacuo to a solid and addition of ethyl acetate (145 mL). The amine solution was then added to the solution of the crude product (slight exotherm) resulting in the formation of a precipitate.

Methanol (30 mL) was added and the suspension heated to reflux. Additional methanol was added through the condenser until a clear solution was obtained 40 mL required). Solvent was then allowed to distill off until the solution developed a haze and a small amount of solid was evident. The flask was closed and 3.5 mL of methanol was added through a condenser. The flask was cooled slowly and stirred overnight. The product was filtered and washed with ethyl acetate and hexane and dried under high vacuum. The yield was 11.349 g (81%), 1.1% trans isomer produced.

The foregoing procedure may be repeated with the S-enantiomer under the same conditions.

Method II

18-B.

[1S-[1α,2α(Z),3α,4α]]-7-[3-(Hydroxymethyl)-7-oxabicyclo[2.2.1]hept-2-yl]-5-heptenoic acid, 1-adamantanamine (1:1) salt To a 2-liter, 3-necked round bottom flask maintained under a nitrogen atmosphere and equipped with a mechanical stirrer and two addition funnels was charged (4-carboxybutyl)triphenylphosphonium bromide (130.3 g, 294.1 mmol, Aldrich), tetrahydrofuran (50 mL) and 1,3-Dimethyl-3,4,5,6-tetrahydro-2(1H)-pyrimidinone (DMPU) (71.15 mL, 588.4 mmol). To an addition funnel was charged the S-enantiomer of compound 17-A (25.0 g, 147.1 mmol) and tetrahydrofuran (200 mL). The flask was cooled to 0° C. and a solution of 1 M potassium t-butoxide in tetrahydrofuran (588.5 mL, 588.5 mmol) was added rapidly via the second addition funnel, which was subsequently replaced with an internal thermometer. The reaction mixture was stirred at 0° C. for 0.5 hours and then the cooling bath was removed for 1 hour, final temperature 21° C. The flask was cooled to 0° C. and slowly over 70 minutes was added the S-enantiomer solution and the addition funnel was rinsed with an addition 25 ml tetrahydrofuran. Completion of the reaction was determined by thin layer chromatography (8:1 methylene chloride/methanol) as soon as the rinse was complete. The reaction was quenched 15 minutes after the rinse by the rapid addition of acetic acid via syringe.

The reaction was allowed to warm to room temperature. Water (1500 mL) and ethyl acetate (750 mL) were added at pH 5.77. The pH was adjusted to 13.0 by the slow addition of 10 N sodium hydroxide (51 mL) and fell to 10.72 in 5 minutes. The phases were split and the rich aqueous phase was washed with 1×750 mL ethyl acetate and 1×750 mL of methyl isobutyl ketone (MIBK). To the rich aqueous phase was added MIBK (750 mL) and concentrated hydrochloric acid (100 mL) to pH 0.88. This mixture was stirred for 10 minutes, the phases were split, and the aqueous phase was extracted with an additional 500 mL of MIBK. The MIBK layers were combined and washed with water [1×500 mL, 1×300 mL with 200 mL brine and ethanol (25 mL)]. It took about 12 hours of settling time to effect a clean phase split.

The MIBK-rich phase was placed in a 3-necked, 5-liter round bottomed flask equipped with an overhead stirrer, internal thermometer and still head. The MIBK was dried via an azeotropic distillation of about 20" Hg at 50° to 70° C. to dryness (by KF), with a reduction in volume of 500 mL. 1-Adamantanamine in MIBK (250 mL and a rinse of 100 mL) was charged via vacuum filtration to the hot solution. The solution was heated to reflux (118° C.) and additional MIBK (150 mL) was added as needed to achieve dissolution. The solution was reduced in volume via distillation to a crystallization volume of about 1400 mL (calculated by high pressure liquid chromatography (HPLC)). The solution was allowed to cool slowly and crystallization was observed at 90° C. The slurry was held for 1 hour at 90° C., 1 hour at 60° C., then allowed to cool slowly to 22° C. and held for 14 hours with stirring. The product was isolated on a 9-cm buchner funnel, washed (2×125 mL) with MIBK, and dried on a filter for 0.5 hours and in vacuo at 40° C. for 5 hours. This procedure isolated 38.87 g (65.1%) of 99.0% pure compound 18-B containing 0.4% trans isomer.

A portion of the first crop of this product (35.0 g) was recrystallized from MIBK (880 mL) to afford 33.29 g (95% recovery) containing 0.3% trans isomer, and 0.4% of an impurity. A second recrystallization was performed using 31.0 g of the recrystallized material using methanol (50 mL) and ethyl acetate (250 mL) to provide 26.03 g (84% recovery) of essentially 100% pure compound 18-B.

The foregoing procedures may be repeated with the R-enantiomer under the same conditions.

18-C.
[1S-[1α,2β(5Z),3β,4α]]-7-[3-(hydroxymethyl)-7-oxabicyclo[2.2.1]hept-2-yl]-5-heptenoic acid, methyl ester Acetyl chloride (93.9 mL, 1.33 mol) was slowly added to 2.2 L of methanol at 0° C. The resulting solution was stirred for 30 minutes. Solid compound 18-B was added and the reaction was stirred and allowed to warm to room temperature over 5 hours. The reaction was cooled to 5° C. and triethylamine (38.6 mL, 28 mmol) was added. The mixture was stirred an additional 10 minutes and concentrated in vacuo. The residue was treated with 2 L of water, the pH was adjusted to 2.6, and ethyl acetate (1.5 L) was added. The mixture was shaken and the layers were separated; the aqueous layer was then extracted with additional ethyl acetate (2×1.5 L). The organic extracts were washed with water, saturated bicarbonate solution, water and brine. The organic solution was dried (magnesium sulfate), filtered and concentrated in vacuo to 289.6 g (97%) of the title compound.

TABLE 1

| Example No. | Reaction Time (Hours) | Amount of Product (mg/mL solvents) | Yield (%) | (−)/(+) | Enantiomeric Excess (e.e) % |
| --- | --- | --- | --- | --- | --- |
| 1 | 47 | 1.3 | 65 | 96.8/3.2 | 93.6 |
| 2 | 40 | 1.2 | 60 | 95.9/4.1 | 91.8 |
| 3 | 44 | 1.32 | 66 | 75/25 | 50 |
| 4 | 40 | 1.4 | 70 | 98/2 | 96 |
| 5 | 48 | 1.3 | 65 | 97/3 | 94 |
| 6 | 42 | 1.25 | 62 | 70/30 | 40 |

TABLE 1

| Example No. | Reaction Time (Hours) | Amount of Product (mg/mL solvents) | Yield (%) | (−)/(+) | Enantiomeric Excess (e.e) % |
| --- | --- | --- | --- | --- | --- |
| 7a | 26 | 6.67 | 89 | 99.5/0.5 | 99 |
| 7b | 27 | 6.15 | 82 | 99.5/0.5 | 99 |
| 8 | 17 | 1.28 | 64 | 76/24 | 52 |
| 9 | 17 | 1.34 | 67 | 97.9/2.1 | 95.8 |
| 10 | 16 | 1.48 | 74 | 99.3/0.7 | 98.6 |
| 11 | 16 | 1.6 | 80 | 99.5/0.5 | 99 |
| 12 | 18 | 1.50 | 75 | 91/9 | 82 |
| 13 | 24 | 1.40 | 70 | 70/30 | 40 |

TABLE 3

Reusability of Immobilized Enzyme for Asymmetric Hydrolysis of Diacetate Ester:

| Cycle No. | Reaction Time (Hours) | Amount of Product (mg/mL solvents) | Yield (%) | (−)/(+) | Enantiomeric Excess (e.e) % |
| --- | --- | --- | --- | --- | --- |
| 1 | 19 | 2.27 | 75.6 | 99.5 | 99 |
| 2 | 19 | 2.24 | 74.6 | 99.5 | 99 |
| 3 | 19 | 2.20 | 73.3 | 99.5 | 99 |
| 4 | 19 | 2.19 | 73 | 99.5 | 99 |

Reaction mixture in 40 mL volume contained 36 mL of 50 mM phosphate buffer, pH 7.0, 120 mg of (exo,exo)-7-oxabicyclo(2.2.1)heptane-2,3-dimethanol, diacetate ester, and 60 mg of Pseudomonas lipase P-30 (Amano International, USA) immobilized on Accurel polypropylene. The reaction was conducted at 4° C. in a pH stat. The product formed was (−)-(exo,exo)-7-oxabicyclo(2.2.1)heptane-2,3-dimethanol, monoacetate ester.

What is claimed is:

1. A process for preparing a compound of the formula

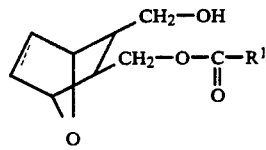

which comprises hydrolyzing a substrate of the formula

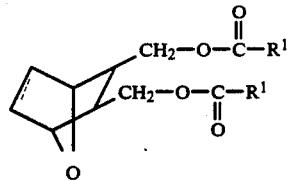

in the presence of one or more water-soluble enzymes or microorganisms capable of selectively hydrolyzing one —O—C(O)—R$^1$ group, wherein:
  (1) the treatment is carried out in a biphasic solvent system comprising an aqueous phase having the enzymes or microorganisms and an organic phase immiscible in water having the substrate; and
  (2) R is alkyl, aryl, cycloalkyl, cycloalkylalkyl, aralkyl or alkaryl.

2. The process of claim 1 wherein the water-soluble enzymes or microorganisms are selected from the group consisting of lipases, esterases, α-chymotrypsin, pancreatin, and microorganisms capable of supplying such enzymes.

3. The process of claim 1, wherein the hydrolysis is carried out in the presence of Pseudomonas lipase or microorganisms from genus Pseudomonas.

4. The process of claim 1, wherein the organic phase comprises a solvent selected from toluene, cyclohexane, xylene, and trichlorotrifluoroethane.

5. The process of claim 1, wherein the aqueous phase comprises an aqueous solvent selected from water, deionized water and aqueous buffer solutions.

6. The process of claim 1, wherein the biphasic solvent system comprises from about 10 to 90 percent by volume of the organic phase comprising the substrate.

7. The process of claim 1, wherein the biphasic solvent system comprises about 20 percent by volume the organic phase and about 80 percent by volume the aqueous phase.

8. The process of claim 1, wherein the substrate to be hydrolyzed is present within the organic phase in an amount of from about 0.1 to about 100 milligrams of the substrate per milliliter of the biphasic solvent.

9. The process of claim 1, wherein the one or more enzymes are present within the aqueous phase in an amount of from about 1 to about 100 units of the enzyme per milligram of the substrate to be hydrolyzed.

10. A process for preparing a product of the formula

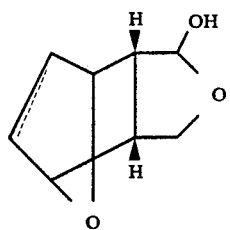

which comprises:
(a) hydrolyzing a substrate of the formula

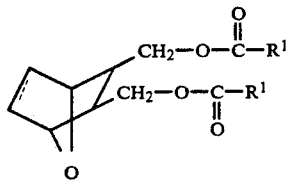

in the presence of one or more water-soluble enzymes or microorganisms capable of selectively hydrolyzing one —O—C(O)—R$^1$ group, wherein:
(1) the treatment is carried out in a biphasic solvent system comprising an aqueous phase having the enzymes or microorganisms and an organic phase immiscible in water having the substrate; and
(2) R$^1$ is alkyl, aryl, cycloalkyl aralkyl, cycloalkylalkyl, or alkaryl.
to form a hydroxyl intermediate of the formula

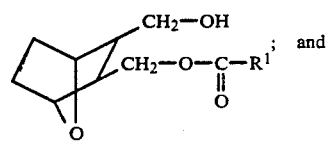; and (b) oxidizing the hydroxyl intermediate to form a first aldehyde of the formula

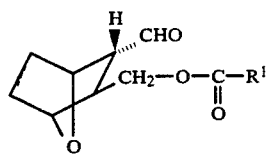

or a second aldehyde of the formula

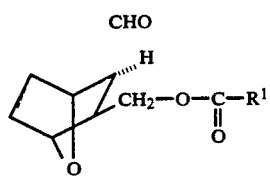

or a mixture of the first and the second aldehyde;
(c) hydrolyzing the aldehydes to form the product.

11. The process of claim 10, further comprising hydrogenating the substrate, the hydroxyl intermediate, the aldehyde or aldehydes or the product if a double bond is present to form a saturated product.

12. A process for preparing [1S-[1α2,α(Z), 3α,4α[[-7-[3[[[[(1-oxoheptyl)amino]acetyl]amino]methyl]-7-oxabicyclo-[2.2.1]hept-2-yl]-5-heptenoic acid, which comprises:
(a) hydrolyzing a substrate of the formula

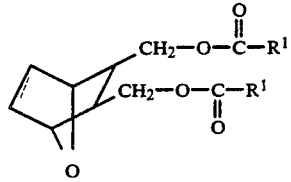

in the presence of one or more water-soluble enzymes or microorganisms capable of selectively hydrolyzing an —O—C(O)—R$^1$ group, wherein R$^1$ is alkyl, aryl, cycloalkyl, aralkyl, cycloalkylalkyl or alkaryl and the treatment is carried out in a biphasic solvent system comprising an aqueous phase having the enzymes or microorganisms and an organic phase immiscible in water having the substrate and forms a hydroxyl intermediate of the formula

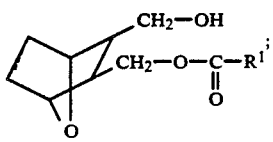

(b) oxidizing the hydroxyl intermediate to form a first aldehyde of the formula

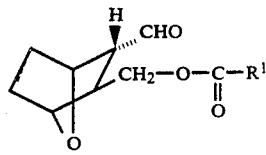

or a second aldehyde of the formula

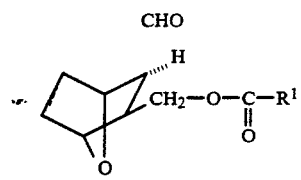

or a mixture of the first and the second aldehyde;

(c) hydrolyzing the aldehyde or aldehydes to form a furanol intermediate of the formula

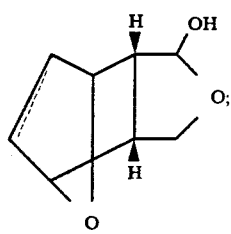

(d) alkylating and acidifying the furanol intermediate to form a pyranol intermediate of the formula

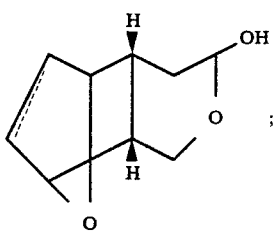

hydrogenating the substrate, the aldehydes, the hydroxyl, the furanol or the pyranol intermediate if a double bond is present;

(f) decyclizing and alkylating the pyranol intermediate to form a carboxyl intermediate of the formula

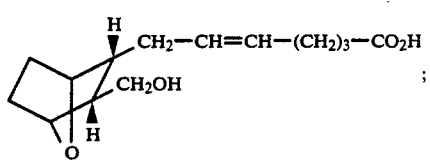

(g) esterifying the carboxyl intermediate to form an ester of the formula

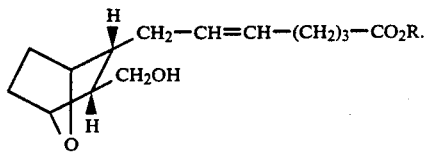

wherein R is alkyl, aryl, cycloalkyl, cycloalkylalkyl, aralkyl, or alkaryl;

(h) reacting the ester with an activating reagent and an aminating reagent, followed by a base to form a diacid of the formula

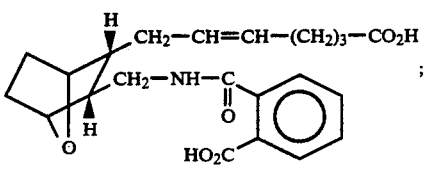

(i) hydrolyzing the diacid with water and an aqueous acid in the presence of an organic co-solvent with heating at reflux to form an amino acid of the formula

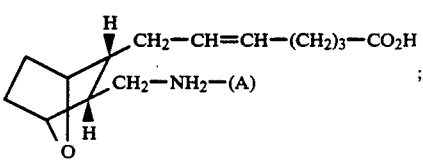

wherein A is a conjugate acid; and (j) acylating the amino acid with [(1-oxoheptyl)amino]acetic acid in the presence of a coupling agent and a tertiary amine base to form [1S-[1α,2α(Z),3α,4α]]-7-[3[[[[(1-oxoheptyl)amino]acetyl]amino]methyl-7-oxabicyclo[2.2.1]hept-2-yl]-5-heptenoic acid.

13. The process of claim 12, further comprising neutralizing the amino acid prior to the acylation.

14. The process of claim 12, wherein the carboxyl intermediate is prepared by treating the pyranol with an ylide of the formula $$Ph_3P=CH(CH_2)_3CO_2 \ominus M \oplus$$

in tetrahydrofuran wherein Ph is phenyl and M⊕ is hydrogen or an alkali metal ion.

15. The process of claim 14, wherein the phosphine is prepared in situ by treating $$Ph_3P\oplus(CH_2)_4CO_2H$$

Halo⊖ wherein halo is fluoro, chloro, bromo, or iodo, with an alkali metal butoxide, amylate, hydride or disilazide.

16. The process of claim 12, wherein the carboxyl intermediate is esterified by first aminating the carboxyl intermediate to form an amine salt, then treating with an alcohol ROH in the presence of an acid.

* * * * *